United States Patent [19]
Goldsworthy et al.

[11] Patent Number: 6,103,222
[45] Date of Patent: Aug. 15, 2000

[54] COSMETIC COMPOSITIONS

[75] Inventors: Maxine Jane Goldsworthy, London; David Andrew Jakubovic, Staines; Martin Ian James, Camberley; James Joseph Scally, Egham; Andrew David Watson, Redhill, all of United Kingdom

[73] Assignee: The Procter & Gamble Company

[21] Appl. No.: 09/077,652

[22] PCT Filed: Nov. 22, 1996

[86] PCT No.: PCT/US96/18672

§ 371 Date: Jun. 2, 1998

§ 102(e) Date: Jun. 2, 1998

[87] PCT Pub. No.: WO97/20540

PCT Pub. Date: Jun. 12, 1997

[30] Foreign Application Priority Data

Dec. 2, 1995 [GB] United Kingdom .................... 9524717

[51] Int. Cl.⁷ .............................. A61K 7/021; A61K 7/06
[52] U.S. Cl. ................................ 424/63; 424/69; 424/70.1
[58] Field of Search .......................................... 424/63, 69

[56] References Cited

U.S. PATENT DOCUMENTS

| | | | |
|---|---|---|---|
| 3,444,291 | 5/1969 | Bivans | 424/63 |
| 3,978,207 | 8/1976 | Fotiu et al. | 424/63 |
| 4,486,405 | 12/1984 | Klein | 424/59 |
| 4,659,562 | 4/1987 | Arraudeau et al. | 424/63 |
| 4,804,532 | 2/1989 | Busch, Jr. | 424/69 |
| 5,143,722 | 9/1992 | Hollenberg et al. | 424/63 |

OTHER PUBLICATIONS

Nakamura et al., "Blurring of Wrinkles Through Control of Optical Properties", Preprint of the XIVth I.F.S.C.C. Congress, Barcelona, vol. 1, pp. 51–63 (1986).

*Primary Examiner*—Terressa M. Boykin
*Attorney, Agent, or Firm*—Darryl C. Little

[57] ABSTRACT

The present invention relates to cosmetic compositions in the form of a water-in-oil emulsion comprising:
(a) discontinuous aqueous phase comprising an aqueous or hydroalcoholic solution of acidic skin care active;
(b) continuous oil phase; and
(c) pigment which has been coated with organosilicone component selected from a polyorganosiloxane and a silane, and mixtures thereof;

characterized in that the aqueous phase has a pH of less than about 6 and the coated pigment has a hydrogen potential of less than about 2.0 ml $H_2$/g of coated pigment.

The compositions of the invention provide benefits in terms of reducing hydrogen gas generation and improving product stability.

21 Claims, No Drawings

COSMETIC COMPOSITIONS

FIELD OF THE INVENTION

The present invention relates to cosmetic compositions and more particularly, to pigmented foundation make-up compositions and concealers having anti-acne activity and enhanced product stability.

BACKGROUND OF THE INVENTION

A foundation composition can be applied to the face and other parts of the body to even skin tone and texture and to hide pores, imperfections, fine lines and the like. A foundation composition is also applied to moisturize the skin, to balance the oil level of the skin and to provide protection against the adverse effects of sunlight, wind and the harsh environment.

Make-up compositions are generally available in the form of liquid or cream suspensions, emulsions, gels, pressed powders or anhydrous oil and wax compositions.

U.S. Pat. No. 3,444,291 discloses a method of filling and camouflaging skin cavities by applying a composition which includes 65 to 75 parts by weight of a microcrystalline wax and about 25 to 35 parts of a mineral oil. The composition includes a colourant, preferably a coal tar dye, for example, D &C Red No. 17, which matches the colour of the user's skin.

A spreadable, flowable and greaseless cosmetic cover-up composition is taught in U.S. Pat. No. 4,486,405. That composition is characterized by the presence of a first and a second alkoxylated surfactant present in substantially the same concentration.

U.S. Pat. No. 4,804,532 recites a facial cosmetic powder which utilizes crystalline silica in much lower concentration than that employed in the then prior art compositions. This powder, used as a blush or a facial coating, is said to be effective in hiding skin wrinkles, lines and pores. The composition is a mixture of a colour phase and a diluent phase. The colour phase is formed by blending crystalline silica with colourants. The resultant colour phase is mixed with the diluent phase, essentially formed from nacreous materials such as talc and mica, to form the composition.

The use of a foundation composition which has a significantly high concentration of nacreous material is taught in U.S. Pat. No. 3,978,207. This foundation, a pressed powder composition, is characterized by the presence of a nacreous material such as mica and a binder oil which provides a frosted pearl effect, that is, a lustrous look. The colour of this foundation is provided by the nacreous material.

U.S. Pat. No. 4,659,562 discloses a cosmetic make-up composition which includes, as a binding agent, an intimate mixture of from 5 to 95 weight percent of a mixture of finely divided silica and about 5 to 95 weight percent of finely divided polyethylene fibres. The composition is recited to maintain its uniformity over the areas of the skin to which it is applied. That is, it is said to be "creaseproof". The composition of the '562 patent includes colourant in admixture with nacreous agents.

Nakamura et al., Preprints of the XIVth I.F.S.C.C. Congress, Barcelona, 1986, Vol. I, 51–63 (1986) describes a novel make-up composition utilizing spherical silica and polydimethyl siloxane. This combination is recited to provide a foundation which reduces wrinkle visibility to a greater extent than make-up foundations with which it was compared. This reduction in wrinkle visibility is caused by optical blurring enhanced by the novel use of spherical silica and polydimethyl siloxane.

U.S. Pat. No. 5,143,722 discloses a cosmetic make-up composition comprising water-in-oil emulsions comprising pigment coated with polysiloxane, a silicone phase, a water phase and a polydiorganosiloxane-polyoxyalkylene copolymeric surfactant.

Pigments are incorporated into cosmetic compositions to provide colour, coverage and enhanced skin appearance. For formulation of pigmented cosmetic emulsion compositions it is preferable to incorporate coated pigments. Unlike uncoated pigments, coated pigments, e.g. silicone-coated pigments, have the advantage that they are "wettable" in silicone oils.

Poly(methylhydrogen) siloxanes are known for use as coatings for pigments which are suitable for use in cosmetic compositions. Poly(methylhydrogen) siloxanes contain reactive hydrogen functionalities which provide substantivity to the pigment. However, a common unwanted side reaction of these materials when used in formulations in which water or alcohol is present is nucleophilic attack on residual —Si—H functionality to generate hydrogen gas as shown below:

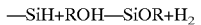

—SiH+ROH—SiOR+$H_2$ where ROH is water or alcohol.

The production of hydrogen gas caused by the above reaction has been known to give rise to undesirable "bubbling" in formulations where pigments coated with silicon hydride-containing polysiloxanes are used in the presence of water or alcohol at acidic pH. The compositions according to the present invention seek to solve this problem.

Since acidic skin care agents such as salicylic acid are most active at low pH (when a high concentration of free acid is present in solution) it would be desirable to deliver the agent from an aqueous phase at a pH at which it exists significantly in protonated form. It is accordingly a primary object of this invention to provide a cosmetic composition comprising a low pH aqueous solution of an acidic skin care active, which at the same time does not give rise to undesirable evolution of hydrogen gas.

It is also an object of the invention to provide a cosmetic composition having improved product stability.

It is a further object of the present invention to provide a cosmetic composition having improved anti-acne activity.

SUMMARY OF THE INVENTION

In accordance with one aspect of the present invention, there is provided a cosmetic composition in the form of a water-in-oil emulsion comprising:

(a) discontinuous aqueous phase comprising an aqueous or hydroalcoholic solution of acidic skin care active (b) continuous oil phase; and (c) pigment which has been coated with organosilicon component selected from a polyorganosiloxane or a silane;

characterised in that the aqueous phase has a pH of less than about 6 and the coated pigment has hydrogen potential of less than about 2.0 ml $H_2$/g of coated pigment.

The cosmetic compositions of the present invention provide improved product stability and reduction of hydrogen gas generation.

All levels and ratios are by weight of total composition, unless otherwise indicated. Chain lengths and degrees of alkoxylation are also specified on a weight average basis.

DETAILED DESCRIPTION OF THE INVENTION

The cosmetic composition according to the present invention comprises an aqueous phase comprising an aqueous or hydroalcoholic solution of an acidic skin care active, an oil phase and a coated pigment. The composition is in the form of a water-in-oil emulsion.

A first essential component of the compositions of the present invention is an aqueous or hydroalcoholic solution of an acidic skin care active.

Suitable skin care actives can be selected from hydroxycarboxylic acids. As used herein the term acidic skin care active means any skin care active containing an acidic functional group (e.g. carboxy, sulfonic).

Suitable hydroxycarboxylic acids can be selected from hydroxymonocarboxylic acids having the following chemical structure:

$$R_1(CR_2OH)_m(CH_2)_nCOOH$$

wherein $R_1$, $R_2$=H, alkyl, aralkyl or aryl group of saturated or unsaturated, straight or branched chain or cyclic form, having from 1 to 25 carbon atoms; m=1,2,3,4,5,6,7,8 or 9; n=0 or a numerical number up to 23.

The hydroxymonocarboxylic acid may be present as a free acid, lactone, or salt form. The lactone form could be either inter or intramolecular lactone, however, most common ones are intramolecular lactones with a ring structure formed by elimination of one or more water molecules between a hydroxy group and the carboxylic group. Since the hydroxymonocarboxylic acids are organic in nature, they may form a salt or a complex with an inorganic or organic base such as ammonium hydroxide, sodium or potassium hydroxide, or triethanolamine.

The hydroxymonocarboxylic acid and its related compounds may exist as stereoisomers such as D, L, and DL forms.

Typical alkyl, aralkyl and aryl groups for $R_1$ and $R_2$ include methyl, ethyl, propyl, isopropyl, benzyl and phenyl. The hydrogen atoms of the $R_1$ and $R_2$ and $(CH_2)_n$ may be substituted by a nonfunctional element such as F, Cl, Br, I, S or a radical such as a lower alkyl or alkoxy, saturated or unsaturated, having 1 to 9 carbon atoms. Representative hydroxymonocarboxylic acids are 2-hydroxyacetic acid (glycolic acid), 2-hydroxypropanoic acid (lactic acid), 2-methyl 2-hydroxypropanoic acid (methyllactic acid), 2-hydroxybutanoic acid, phenyl 2-hydroxyacetic acid (mandelic acid), phenyl 2-methyl 2-hydroxyacetic acid, 3-phenyl 2-hydroxypropanoic acid (phenyllactic acid), 2,3-dihydroxypropanoic acid (glyceric acid), 2.3.4-trihydroxybutanoic acid, 2,3,4,5-tetrahydroxypentanoic acid, 2,3,4,5,6-pentahydroxyhexanoic acid, 2-hydroxydodecanoic acid (alpha hydroxylauric acid), 2,3,4,5,6,7-hexahydroxyheptanoic acid, diphenyl 2-hydroxyacetic acid (benzilic acid), 4-hydroxymandelic acid, 4-chloromandelic acid, 3-hydroxybutanoic acid, 4-hydroxybutanoic acid, 2-hydroxyhexanoic acid, 5-hydroxydodecanoic acid, 12-hydroxydodecanoic acid, 10-hydroxydecanoic acid, 16-hydroxyhexadecanoic acid, 2-hydroxy-3-methylbutanoic acid, 2-hydroxy-4-methylpentanoic acid, 3-hydroxy-4-methoxymandelic acid, 4-hydroxy-3-methoxymendelic acid, 2-hydroxy-2-methylbutanoic acid, 3-(2-hydroxyphenyl) lactic acid, 3-(4-hydroxyphenyl) lactic acid, hexahydromandelic acid, 3-hydroxy-3-methylpentanoic acid, 4-hydroxydecanoic acid, 5-hydroxydecanoic acid and aleuritic acid.

Another type of hydroxyacid suitable for use herein is a hydroxydicarboxylic acid having the following formula:

$$HOOC(CHOH)_m(CH_2)_nCOOH$$

wherein m=1,2,3,4,5,6,7,8 or 9: n=0 or an integer up to 23.

The hydroxydicarboxylic acid may also be present as a free acid, lactone or salt form. The hydroxydicarboxylic acid and its related compounds may also exist as stereoisomers such as D, L, DL and meso forms.

The hydrogen attached to the carbon atom may be substituted by a nonfunctional element such as F, Cl, Br, I, S, or a radical such as a lower saturated or unsaturated alkyl or alkoxy having from 1 to 9 carbon atoms.

Representative hydroxydicarboxylic acids are 2-hydroxypropanedioic acid (tartronic acid), 2-hydroxybutanedioic acid (malic acid), erythraric acid and threaric acid (tartaric acid), arabiraric acid, ribaric acid, xylaric acid and lyxaric acid, glucaric acid (saccharic acid), galactaric acid (mucic acid), mannaric acid, gularic acid, allaric acid, altraric acid, idaric acid and talaric acid.

A third type of hydroxyacid suitable for use herein is a miscellaneous group of compounds which is not readily represented by the above generic structure of either the first type or the second type described above. Included in the third type of hydroxyacids are the following:

Hydroxycarboxylic acids of formula:

$$R(OH)_m(COOH)_n$$

wherein m, n=1,2,3,4,5,6,7,8 or 9, R=H, alkyl, aralkyl or aryl group of saturated or unsaturated, straight or branched chain or cyclic form, having from 1 to 25 carbon atoms; citric acid, isocitric acid, citramalic acid, agaricic acid (n-hexadecylcitric acid), quinic acid, uronic acids including glucuronic acid, glucuronolactone, galacturonic acid, galacturonolactone, hydroxypyruvic acid, hydroxypyruvic acid phosphate, ascorbic acid, dihydroascorbic acid, dihydroxytartaric acid, 2-hydroxy-2-methylbutanoic acid, 1-hydroxy-1-cyclopropane carboxylic acid, 2-hydroxyhexanedial, 5-hydroxylysine, 3-hydroxy-2-aminopentanoic acid, tropic acid, 4-hydroxy-2,2-diphenylbutanoic acid, 3-hydroxy-3-methylglutaric acid, and 4-hydroxy-3-pentenoic acid.

The third type of hydroxyacid may also be present as a free acid, lactone or salt form and may also exist as stereoisomers such as D, L, DL and meso forms.

The hydrogen atom attached to the carbon atom may be substituted by a nonfunctional element such as F, Cl, Br, I, S or a radical such as a lower saturated or unsaturated alkyl or alkoxy having from 1 to 9 carbon atoms.

Mixtures of hydroxy acids can also be used in the compositions herein. Hydroxy acids are useful herein from the viewpoint of reducing wrinkles and improving skin feel and appearance.

Other suitable hydroxy acids for use herein include salicylic acid, retinoic acid, and azelaic acid.

Preferred acidic skin care actives for use herein include salicylic acid, retinoic acid, azelaic acid, lactic acid, glycolic acid, pyruvic acid, and mixtures thereof, more preferably salicylic acid and azelaic acid, and especially salicylic acid. The salicylic acid is useful herein as an anti-acne active.

The acidic skin care active is present at a level of from about 0.1% to about 10%, preferably from about 0.1% to about 5%, more preferably from about 0.5% to about 3%, by weight of composition.

The acidic skin care active is solubilized in water or a hydroalcoholic solution, for example, solutions based upon $C_2$–$C_6$ alcohols, diols and polyols, preferred alcohols being selected from ethanol, dipropylene glycol, butylene glycol, hexylene glycol, and mixtures thereof. Alcohol is preferably present in the compositions herein at a level of from about 1% to about 20%. The final aqueous/hydroalcoholic skin care active solution preferably has a pH at ambient temperature (25° C.) of less than about $pK_a+1$, where $pK_a$ is the logarithmic acidity constant for the fully protonated skin care active. In preferred embodiments, the pH of the final solution is less than about $pK_a$.

The logarithmic acidity constant is thus defined by reference to the equilibrium $$H^+ + H_{n-1}A = H_nA$$

where $H_nA$ is the fully protonated acid, n is the number of protons in the fully protonated acid and $H_{n-1}A$ is the conjugate base of the acid corresponding to loss of one proton.

The acidity constant for this equilibrium is therefore $$K_n = \frac{[H_nA]}{[H^+][H_{n-1}A]}$$

and $pK_a = \log_{10} K_n$

For the purposes of this specification, acidity constants are defined at 25° C. and at zero ionic strength. Literature values are taken where possible (see Stability Constants of Metal-Ion Complexes, Special Publication No. 25, The Chemical Society, London); where doubt arises they are determined by potentiometric titration using a glass electrode.

The $pK_a$ of the acidic skin care active used herein is preferably in the range of from about 1 to about 5.5, more preferably from about 2 to about 4.5, especially from about 2 to about 4.

The pH of the aqueous phase is less than about pH 6, preferably from about pH 2 to about pH 5, more preferably from about pH 2.5 to about pH 4. At pH values of less than about 5 the aqueous phase is preferably free of acid labile species such as polyacrylic or polymethacrylic acids or esters.

The compositions of the present invention can also comprise a solubilizing agent for solubilizing the acidic skin care active. Preferably the solubilizing agent herein is selected from pyrrolidone-based solubilising agents, polyethylene glycol based nonionic surfactants having an HLB of greater than about 15, preferably greater than about 18, and mixtures thereof. The solubilizing agent herein is preferably present at a level of from about 0.1% to about 10%, more preferably from about 0.1% to about 5%, especially from about 0.5% to about 2% by weight of composition.

Pyrrolidone-based solubilising agents suitable for use herein include polyvinylpyrrolidone or $C_1$–$C_4$ alkyl polyvinylpyrrolidone having a molecular weight (viscosity average) in the range from about 1500 to about 1,500,000, preferably from about 3000 to about 700,000, more preferably from about 5000 to about 100,000. Suitable examples of pyrrolidone-based solubilising agents are polyvinylpyrrolidone (PVP) (or povidone) and butylated polyvinylpyrrolidone. The most preferred pyrrolidone-based solubilising agent herein is polyvinylpyrrolidone. PVP is commercially available under the trade name Luviskol (RTM) from BASF. A preferred PVP solubilising agent herein is Luviskol K17 which has a viscosity-average molecular weight of about 9,000. Other pyrrolidone-based solubilising agents for use herein include $C_1$–$C_{18}$ alkyl or hydroxyalkyl pyrrolidones such as lauryl pyrrolidone.

The pyrrolidone-based solubilising agent is preferably present in the composition herein in a level of from about 0.1% to about 10%, more preferably from about 0.1% to about 5%, especially from about 0.5% to about 2% by weight of composition. The weight ratio of acidic skin care active:pyrrolidone-based solubilising agent is preferably in the range from about 10:1 to about 1:10, more preferably from about 5:1 to about 1:5.

Preferred embodiments of the invention additionally comprise from about 0.01% to about 5% by weight of an additional acid or salt thereof which is soluble in water at pH values of less than or equal to the $pK_a$ of the corresponding acid, for example, an acid selected from citric acid, boric acid, and salts, and mixtures thereof. These materials are valuable herein in combination with the pyrrolidone-based complexing agent from the viewpoint of aiding solubilization of the acidic skin care active. Particularly preferred herein from this viewpoint is a sodium salt of citric acid. In preferred embodiments, the acid or salt thereof is soluble to a level of at least 5% w/w at 25° C.

The composition of the present invention is in the form of a water-in-oil emulsion, wherein in preferred embodiments the oil phase comprises a mixture of volatile silicones and non-volatile silicones. The silicone fluid is present in an amount of from about 1% to about 50% by weight. Suitable volatile silicones include cyclic and linear volatile polyorganosiloxanes. The term "nonvolatile" as used herein shall mean that the material exhibits very low or no significant vapor pressure at ambient conditions, as is understood by those in the art. In general, this will mean no more than 0.2 mm Hg at one atmosphere and 25° C.

A description of various volatile silicones is found in Todd, et al. "Volatile Silicone Fluids for Cosmetics", 91 *Cosmetics and Toiletries* 27–32 (1976).

Preferred cyclic silicones include polydimethylsiloxanes containing an average of from about 3 to about 9 silicon atoms, preferably from about 4 to about 5 silicon atoms. Preferred linear silicones include the polydimethylsiloxanes containing an average of from about 3 to about 9 silicon atoms. The linear volatile silicones generally have viscosities of less than about 5 centistokes at 25° C., while the cyclic materials have viscosities of less than about 10 centistokes. Examples of silicone oils useful in the present invention include: Dow Corning 344, Dow Corning 21330, Dow Corning 345, and Dow Corning 200 (manufactured by the Dow Corning Corporation): Silicone 7207 and Silicone 7158 (manufactured by the Union Carbide Corporation). SF:202 (manufactured by General Electric) and SWS-03314 (manufactured by Stauffer Chemical).

Suitable non-volatile silicones preferably have an average viscosity of from about 1,000 to about 2,000,000 $mm^2.s^{-1}$ at 25° C. more preferably from about 10,000 to about 1,800,000 $mm^2.s^{-1}$, even more preferably from about 100,000 to about 1,500,000 $mm^2.s^{-1}$. Lower viscosity non-volatile silicone conditioning agents, however, can also be used. Viscosity can be measured by means of a glass capillary viscometer as set forth in Dow Corning Corporate Test Method CTM0004, Jul. 20, 1970. Suitable non-volatile silicone fluids for use herein include polyalkyl siloxanes, polyaryl siloxanes, polyalkylaryl siloxanes, polysiloxanes with amino functional substitutions, polyether siloxane copolymers, and mixtures thereof. The siloxanes useful in the present invention may be endcapped with any number of moieties, including, for example, methyl, hydroxyl, ethylene oxide, propylene oxide, amino and carboxyl. However, other silicone fluids having skin conditioning properties may be used. The non-volatile polyalkyl siloxane fluids that may be used include, for example, polydimethylsiloxanes. These siloxanes are available, for example, from the General Electric Company as a Viscasil (RTM) series and from Dow Corning as the Dow Corning 200 series. Preferably, the viscosity ranges from about 10 $mm^2.s^{-1}$ to about 100,000 mm$^2$.s$^{-1}$ at 25° C. The polyalkylaryl siloxane fluids that may be used, also include, for example, polymethylphenylsiloxanes. These siloxanes are available, for example, from the General Electric Company as SF 1075 methyl phenyl fluid or from Dow Corning as 556 Cosmetic Grade Fluid. The polyether siloxane copolymer that may be used includes, for example, a polypropylene oxide modified dimethylpolysiloxane (e.g., Dow Corning DC-1248) although ethylene oxide or mixtures of ethylene oxide and propylene oxide may also be used.

References disclosing suitable silicone fluids include U.S. Pat. No. 2,826,551, Green; U.S. Pat No. 3,964,500, Drakoff, issued Jun. 22, 1976; U.S. Pat. No. 4,364,837, Pader; and GB-A-849,433, Woolston. In addition, *Silicone Compounds* distributed by Petrarch Systems Inc., 1984 provides an extensive (though not exclusive) listing of suitable silicone fluids.

Preferred non-volatile silicones for use herein include polydiorganosiloxane-polyoxyalkylene copolymers containing at least one polydiorganosiloxane segment and at least one polyoxyalkylene segment, said polydiorganosiloxane segment consisting essentially of

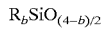

siloxane units wherein b has a value of from about 0 to about 3, inclusive, there being an average value of approximately 2 R radicals per silicon for all siloxane units in the copolymer, and R denotes a radical selected from methyl, ethyl, vinyl, phenyl and a divalent radical bonding said polyoxyalkylene segment to the polydiorganosiloxane segment, at least about 95% of all R radicals being methyl; and said polyoxyalkylene segment having an average molecular weight of at least about 500, preferably at least about 1000 and consisting of from about 0 to about 50 mol percent polyoxypropylene units and from about 50 to about 100 mol percent polyoxyethylene units, at least one terminal portion of said polyoxyalkylene segment being bonded to said polydiorganosiloxane segment, any terminal portion of said polyoxyalkylene segment not bonded to said polydiorganosiloxane segment being satisfied by a terminating radical; the weight ratio of polydiorganosiloxane segments to polyoxyalkylene segments in said copolymer having a value of from about 2 to about 8. Such polymers are described in U.S. Pat. No. 4,268,499.

More preferred for use herein are polydiorganosiloxane-polyoxyalkylene copolymers having the general formula:

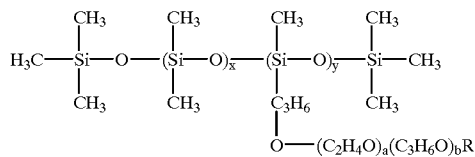

wherein x and y are selected such that the weight ratio of polydiorganosiloxane segments to polyoxalkylene segments is from about 2 to about 8, the mol ratio of a:(a+b) is from about 0.5 to about 1, and R is a chain terminating group, especially selected from hydrogen; hydroxyl; alkyl, such as methyl, ethyl, propyl, butyl, benzyl; aryt, such as phenyl; alkoxy such as methoxy, ethoxy, propoxy, butoxy; benzyloxy; aryloxy, such as phenoxy; alkenyloxy, such as vinyloxy and allyloxy; acyloxy, such as acetoxy, acryloxy and propionoxy and amino, such as dimethylamino.

The number of and average molecular weights of the segments in the copolymer are such that the weight ratio of polydiorganosiloxane segments to polyoxyalkylene segments in the copolymer is preferably from about 2.5 to about 4.0.

Suitable copolymers are available commercially under the tradenames Belsil (RTM) from Wacker-Chemie GmbH, Geschaftsbereich S, Postfach D-8000 Munich 22 and Abil (RTM) from Th. Goldschmidt Ltd,. Tego House, Victoria Road, Ruislip, Middlesex, HA4 OYL. Particularly preferred for use herein are Belsil (RTM) 6031, Abil (RTM) B88183, DC3225C, DC5200, Abil We09 and Abil EM90. A preferred silicone herein is known by its CTFA designation as dimethicone copolyol.

The silicone oil phase preferably comprises from about 2% to about 25%, more preferably from about 5% to about 15% by weight of composition of non-volatile silicones.

A third essential component of the present invention is a pigment which has been coated with organosilicon component selected from a polyorganosiloxane or a silane wherein the coated pigment has a hydrogen potential of less than about 2.0, preferably less than about 1.0, more preferably less than about 0.5 ml, and especially less than about 0.1 ml H$_2$/g of coated pigment. The pigment used herein is in particulate form. The pigment is incorporated into the continuous oil phase in the compositions herein. The coatings used can be bonded to the pigment surface by covalent bonding, physical adsorption or adhesion, preferably by covalent bonding to the surface of the pigment. The function of the coatings herein is to hydrophobically-modify the pigments so that thay are "wettable" in the continuous silicone phase of the water-in-silicone emulsions. The coated pigment is also useful herein from the viewpoint of reducing hydrogen gas evolution and improving product stability.

Without wishing to be limited by theory it is believed that although the pigments are present in the oil phase of the water-in-oil emulsion, hydrogen ions from the aqueous phase can pass through the interface of the emulsion into the oil phase, where they are available to react with the pigment coatings, e.g. to give off hydrogen gas. However, by using organosilicon-coated pigments having a hydrogen potential of less than about 2 ml H$_2$/g of coated pigment, hydrogen gas generation is reduced.

The hydrogen potential of the coated pigment is measured herein using the following test method:

A dispersion of the coated pigment containing 20 g of coated pigment is placed in a flask on a magnetic stirrer and 100 ml of a 2% ethanolic solution of potassium hydroxide is added with stirring at ambient temperature. The hydrogen gas which is evolved is collected in a second flask at ambient temperature and pressure (25° C., 1 At). The hydrogen gas released can therefore be volumetrically measured.

A wide variety of organosilicon components can be used for treating the pigments herein. A suitable polyorganosiloxane herein is selected from:

(A) material of the formula:

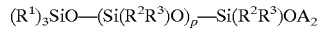

wherein p is 1 to 1000, preferably from 1 to 100, A$_2$ is hydrogen or an alkyl group having from 1 to 30 carbon atoms, R$^1$ is a C$_1$–C$_{30}$ alkyl, preferably methyl, R$^2$ and R$^3$ are independently selected from a C$_1$–C$_{30}$ alkyl and a phenyl, preferably wherein R$^2$ and R$^3$ are both methyl or wherein R$^2$ is methyl and R$^3$ is phenyl; or (B) material of the formula:

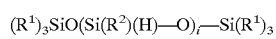

wherein i is 1 to 1000, preferably 1 to 100, and wherein $R^1$ and $R^2$ are as defined above for formula (A).

In preferred embodiments the organosilicon component is selected from a silane. The silane can be selected from material of the formula:

$$A_1SiX_1X_2X_3 \tag{C}$$

wherein A is an alkyl or alkenyl group having from 1 to 30 carbon atoms, and $X_1$, $X_2$ and $X_3$ are independently $C_1$–$C_4$ alkoxy preferably methoxy or ethoxy, or halo, preferably chloro.

When the pigment herein is treated with silane material having the formula (C) described herein above a pigment having the following formula (1) is produced:

$$P\text{—}O\text{—}Si(OH)(A)\text{—}[\text{—}O\text{—}Si(OH)(A)\text{—}]_{0-100}\text{—}OH$$

wherein P is an atom in the pigment surface and each A is an alkyl or alkenyl group having up to 30 carbon atoms. A number of adjacent polysiloxane chains as shown in formula (1) can be cross-linked through oxygen atoms to form a polysiloxane chain with up to 100 repeating —Si(—OP)—O-units that extend along the pigment surface, in addition to the polysiloxane chain which extends away from the pigment surface. Examples of linear or branched alkyl groups are methyl, ethyl, propyl, butyl, pentyl, hexyl, heptyl, octyl, and so forth up to octadecyl. "Alkenyl" includes carbon chains with one or more double bonds; examples of such groups include ethylene, propylene, acrylyl, methacrylyl, and residues of unsaturated fatty acids such as oleic ($C_{17}C_{33}$–), linoleic ($C_{17}H_{31}$–), and linolenic ($C_{17}H_{29}$–).

When the pigment herein is treated with polyorganosiloxane material having the formula (A) described hereinabove a pigment having the following formula (2) is produced:

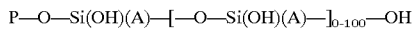

$$P\text{—}O\text{—}(Si(R^2R^3)O)_p\text{—}Si(R^1)_3 \tag{2}$$

wherein p is 1–1000, preferably 1 to 100, $R^1$, $R^2$ and $R^3$ are as defined above for formula (A) and P is an atom in the pigment surface.

When the pigment herein is treated with polyorganosiloxane material having the formula (B) described hereinabove a pigment having the following formula (3) is produced:

$$(R^1)_3SiO\text{—}[Si(R^2)(\text{—}OP)\text{—}O\text{—}]_p\text{—}Si(R^1)_3 \tag{3}$$

wherein each P is an atom in the pigment surface, p is from 1 to 1000, preferably from 1 to 100, $R^1$ and $R^2$ are as defined above in formula (B) and in which each of the up to 100 repeating (Si—O) units is bonded through an oxygen atom to the pigment surface.

The pigment (or a mixture of two or more pigments) can be coated by placing it in dry, finely divided form in a mixer, adding the organosilicon component, and mixing. The organosilicon coating is preferably present at a level of from about 0.01% to about 5%, more preferably from about 0.1% to about 4%, and especially from about 0.5% to about 2%, by weight of the organosilicon coated pigment.

The most preferred coated pigment from the viewpoint of reducing hydrogen gas evolution and improving product stability is Cardre 70429.

Suitable pigments for use herein can be inorganic and/or organic. Also included within the term pigment are materials having a low colour or lustre such as matte finishing agents, and also light scattering agents. Examples of suitable pigments are iron oxides, rutile titanium dioxide, anatase titanium dioxide, ferric oxide, ferrous oxide, chromium oxide, chromuim hydroxide, manganese violet, acylglutamate iron oxides, ultramarine blue, D&C dyes, carmine, and mixtures thereof. Depending upon the type of make-up composition, eg. foundation or blusher, a mixture of pigments will normally be used.

The foundation composition can also include at least one matte finishing agent. (The term matte finishing agents is included within the term pigment). The function of the matte finishing agent is to hide skin defects and reduce shine. Such cosmetically acceptable inorganic agents, i.e., those included in the CTFA Cosmetic Ingredient Dictionary, Third Ed., as silica, hydrated silica, silicone-treated silica beads, mica, talc, polyethylene, titanium dioxide, bentonite, hectorite, kaolin, chalk, diatomaceous earth, attapulgite, and the like may be utilized. Of particular usefulness as a matte finishing agent is low lustre pigment such as titanated mica (mica coated with titanium dioxide) coated with barium sulfate. Of the inorganic components useful as a matte finishing agent low lustre pigment, talc, polyethylene, hydrated silica, kaolin, titanium dioxide and mixtures thereof are particularly preferred. Materials suitable for use herein as light-scattering agents can be generally described as spherical shaped inorganic materials having a particle size of up to about 100 microns, preferably from about 5 to about 50 microns, for example spherical silica particles. Zinc oxide is not preferred for use in the compositions herein.

Other examples of pigments include lakes of organic colorants such as FD&C Red No. 7 calcium lake, FD&C Yellow No. 5 aluminium lake, D&C Red No. 9 barium lake, and D&C Red No. 30.

The total concentration of the coated pigment may be from about 0.1 to about 25% by weight and is preferably from about 1 to about 15%, more preferably from about 8% to about 12% by weight of the total composition, the exact concentration being dependent to some extent upon the specific mixture of pigments selected for use in a foundation make-up or blusher to achieve the desired shades. The preferred compositions contain from about 2% to about 20% by weight of titanium dioxide and most preferably from about 5% to about 10% by weight of titanium dioxide.

A highly preferred component of the compositions herein is a humectant or mixture of humectants. The humectant or mixture of humectants herein is present in an amount of from about 0.1% to about 30% preferably from about 1% to about 25%, and more preferably from about 1% to about 10% by weight of composition. Suitable humectants are selected from glycerine and polyglycerylmethacrylate lubricant having a viscosity at 25° C. of 300,000 to 1,100,000 cps; a specific gravity at 25° C. of 1 to 1.2 g/ml, a pH of 5.0 to 5.5; a bound water content of 33 to 58%; and, a free water content from 5 to 20%.

The humectant can be incorporated at least partly into the oil phase of the water-in-oil emulsion. The oil phase preferably comprises from about 0.1% to about 10%, more preferably from about 0.1% to about 3% by weight of humectant on a composition basis. The humectant can be introduced into the oil phase in the form of a mixture with or incorporated within a particulate lipophilic or hydrophobic carrier material.

Polyglycerylmethacrylate lubricants having the desired properties are marketed by Guardian Chemical Corporation under the trademark "Lubrajel". The "Lubrajels" identified as "Lubrajel DV", "Lubrajel MS", and "Lubrajel CG" are preferred in the present invention. The gelling agents sold under these trademarks contain about 1% propylene glycol.

Other suitable humectants include sorbitol, panthenols, propylene glycol, dipropylene glycol, butylene glycol, hexylene glycol, alkoxylated glucose derivatives, such as Glucam (RTM) E-20, hexanetriol, and glucose ethers, and mixtures thereof.

The panthenol moisturiser can be selected from D-panthenol ([R]-2,4-dihydroxy-N-[3-hydroxypropyl)]-3,3-dimethylbutamide), DL-panthenol, calcium pantothenate, royal jelly, panthetine, pantotheine, panthenyl ethyl ether, pangamic acid, pyridoxin, pantoyl lactose and Vitamin B complex.

The preferred humectant herein is glycerine. Chemically, glycerine is 1,2,3-propanetriol and is a product of commerce.

The balance of the composition of the present invention is deionized water. The composition preferably comprises from about 20% to about 95%, more preferably from about 40% to about 80% by weight of the oil phase, and from about 5% to about 80%, more preferably from about 20% to about 60% by weight of the water phase.

The make-up compositions of the present invention can also comprise a particulate cross-linked hydrophobic acrylate or methacrylate copolymer. This copolymer is particularly valuable for reducing shine and controlling oil while helping to provide effective moisturization benefits. The cross-linked hydrophobic polymer is preferably in the form of a copolymer lattice with at least one active ingredient dispersed uniformly throughout and entrapped within the copolymer lattice. Alternatively, the hydrophobic polymer can take the form of a porous particle having a surface area ($N_2$-BET) in the range from about 50 to 500, preferably 100 to 300 $m^2$/g and having the active ingredient absorbed therein.

The cross-linked hydrophobic polymer when used herein is in an amount of from about 0.1% to about 10% by weight and is preferably incorporated in the external silicone-containing oil phase. The active ingredient can be one or more or a mixture of skin compatible oils, skin compatible humectants, emollients, moisturizing agents and sunscreens. The polymer material is in the form of a powder, the powder being a combined system of particles. The system of powder particles forms a lattice which includes unit particles of less than about one micron in average diameter, agglomerates of fused unit particles of sizes in the range of about 20 to 100 microns in average diameter and aggregates of clusters of fused agglomerates of sizes in the range of about 200 to 1,200 microns in average diameter.

The powder material of the present invention which can be employed as the carrier for the active ingredient can be broadly described as a cross-linked "post absorbed" hydrophobic polymer lattice. The powder preferably has entrapped and dispersed therein, an active which may be in the form of a solid, liquid or gas. The lattice is in particulate form and constitutes free flowing discrete solid particles when loaded with the active material. The lattice may contain a predetermined quantity of the active material. The polymer has the structural formula:

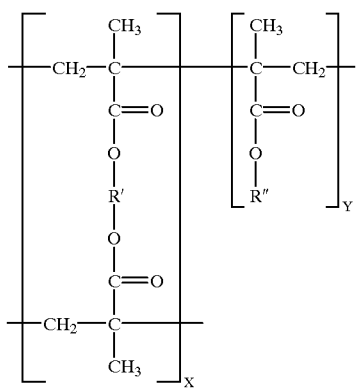

where the ratio of x to y is 80:20, R' is $-CH_2CH_2-$ and R'' is $-(CH_2)_{11}CH_3$.

The hydrophobic polymer is a highly crosslinked polymer, more particularly a highly cross-linked polymethacrylate copolymer. The material is manufactured by the Dow Corning Corporation, Midland, Mich., U.S.A., and sold under the trademark POLYTRAP (RTM). It is an ultralight free-flowing white powder and the particles are capable of absorbing high levels of lipophilic liquids and some hydrophilic liquids while at the same time maintaining a free-flowing powder character. The powder structure consists of a lattice of unit particles less than one micron that are fused into agglomerates of 20 to 100 microns and the agglomerates are loosely clustered into macro-particles or aggregates of about 200 to about 1200 micron size. The polymer powder is capable of containing as much as four times its weight of fluids, emulsions, dispersions or melted solids.

Adsorption of actives onto the polymer powder can be accomplished using a stainless steel mixing bowl and a spoon, wherein the active is added to the powder and the spoon is used to gently fold the active into the polymer powder. Low viscosity fluids may be adsorbed by addition of the fluids to a sealable vessel containing the polymer and then tumbling the materials until a consistency is achieved. More elaborate blending equipment such as ribbon or twin cone blenders can also be employed. The preferred active ingredient for use herein is glycerine. Preferably, the weight ratio of humectant: carrier is from about 1:4 to about 3:1.

Also suitable as a highly cross-linked polymethacrylate copolymer is Microsponges 5647. This takes the form of generally spherical particles of cross-linked hydrophobic polymer having a pore size of from about 0.01 to about 0.05 $\mu$m and a surface area of 200–300 $m^2$/g. Again, it is preferably loaded with humectant in the levels described above.

The compositions of the invention can also contain a hydrophilic gelling agent at a level preferably from about 0.01% to about 10%, more preferably from about 0.02% to about 2%, and especially from about 0.02% to about 0.5%. The gelling agent preferably has a viscosity (1% aqueous solution, 20° C., Brookfield RVT) of at least about 4000 mPa.s, more preferably at least about 10,000 mPa.s and especially at least 50,000 mPa.s.

Suitable hydrophilic gelling agents can generally be described as water-soluble or colloidally water-soluble polymers, and include cellulose ethers (e.g. hydroxyethyl cellulose, methyl cellulose, hydroxypropylmethyl cellulose), polyvinylalcohol, polyquaternium-10, guar gum, hydroxypropyl guar gum and xanthan gum.

Among suitable hydrophilic gelling agents are acrylic acid/alkyl acrylate copolymers and the carboxyvinyl polymers sold by the B.F. Goodrich Company under the trade mark of Carbopol resins. These resins consist essentially of a colloidally water-soluble polyalkenyl polyether crosslinked polymer of acrylic acid crosslinked with from 0.75% to 2.00% of a crosslinking agent such as for example polyallyl sucrose or polyallyl pentaerythritol. Examples include Carbopol 934, Carbopol 940, Carbopol 950, Carbopol 980, Carbopol 951 and Carbopol 981. Carbopol 934 is a water-soluble polymer of acrylic acid crosslinked with about 1% of a polyallyl ether of sucrose having an average of about 5.8 allyl groups for each sucrose molecule. Also suitable for use herein are hydrophobically-modified cross-linked polymers of acrylic acid having amphipathic properties available under the Trade Name Carbopol 1382, Carbopol 1342 and Pemulen TR-1 (CTFA Designation: Acrylates/10–30 Alkyl Acrylate Crosspolymer). A combination of the polyalkenyl polyether cross-linked acrylic acid polymer and the hydrophobically modified cross-linked acrylic acid polymer is also suitable for use herein. Other suitable gelling agents suitable for use herein are oleogels such as trihydroxystearin and aluminium magnesium hydroxy stearate. The gelling agents herein are particularly valuable for providing excellent stability characteristics over both normal and elevated temperatures.

Neutralizing agents suitable for use in neutralizing acidic group containing hydrophilic gelling agents herein include sodium hydroxide, potassium hydroxide, ammonium hydroxide, monoethanolamine, diethanolamine and triethanolamine.

The make-up compositions herein can additionally comprise an emollient. Emollients suitable for the compositions of the present invention include natural and synthetic oils selected from mineral, vegetable, and animal oils, fats and waxes, fatty acid esters, fatty alcohols, alkylene glycol and polyalkylene glycol ethers and esters, fatty acids and mixtures thereof.

Suitable emollients for use herein include, for example, optionally hydroxy-substituted $C_8$–$C_{50}$ unsaturated fatty acids and esters thereof, $C_1$–$C_{24}$ esters of $C_8$–$C_{30}$ saturated fatty acids such as isopropyl myristate, cetyl palmitate and octyldodecylmyristate (Wickenol 142), beeswax, saturated and unsaturated fatty alcohols such as behenyl alcohol and cetyl alcohol, hydrocarbons such as mineral oils, petrolatum and squalane, fatty sorbitan esters (see U.S. Pat. No. 3,988, 255, Seiden, issued Oct. 26 1976), lanolin and lanolin derivatives, such as lanolin alcohol ethoxylated, hydroxylated and acetylated lanolins, cholesterol and derivatives thereof, animal and vegetable triglycerides such as almond oil, peanut oil, wheat germ oil, linseed oil, jojoba oil, oil of apricot pits, walnuts, palm nuts, pistachio nuts, sesame seeds, rapeseed, cade oil, corn oil, peach pit oil, poppyseed oil, pine oil, castor oil, soybean oil, avocado oil, safflower oil, coconut oil, hazelnut oil, olive oil, grapeseed oil, and sunflower seed oil and $C_1$–$C_{24}$ esters of dimer and trimer acids such as diisopropyl dimerate, diisostearylmalate, diisostearyidimerate and triisostearyltrimerate.

Preferred emollients are selected from hydrocarbons such as isohexadecane, mineral oils, petrolatum and squalane, lanolin alcohol, and stearyl alcohol. These emollients may be used independently or in mixtures and may be present in the composition of the present invention in an amount from about 1% to about 30% by weight, and preferably are present in an amount from about 5% to about 15% by weight of the total composition.

The composition may also contain additional materials such as, for example, fragrances, fillers such as nylon, sun-screens, preservatives, electrolytes such as sodium chloride, proteins, antioxidants, chelating agents and water-in-oil emulsifiers as appropriate.

Another optional component of the make-up composition is one or more ultraviolet absorbing agents. Ultraviolet absorbing agents, often described as sunscreening agents, can be present in a concentration in the range of between about 1% and about 12% by weight, based on the total weight of composition. Preferably, the UV absorbing agents constitute between about 2% and 8% by weight. More preferably, the UV absorbing agents can be present in the composition in a concentration range of between about 4% and about 6% by weight. Of the ultraviolet absorbing agents suitable for use herein, benzophenone-3, octyl dimethyl PABA (Padimate O), Parsol MCX, and mixtures thereof are particularly preferred.

Another optional but preferred component herein is one or more additional chelating agents, preferably in the range of from about 0.02% to about 0.10% by weight, based on the total weight of the composition. Preferably, the chelating agent is present in a concentration in the range of between about 0.03% and about 0.07% by weight, based on the total weight of the composition. Among the chelating agents that may be included in the composition is tetrasodium EDTA.

Another optional but preferred component of the foundation composition is one or more preservatives. The preservative concentration in the foundation composition, based on the total weight of that composition, is in the range of between about 0.05% and about 0.8% by weight, preferably between about 0.1% and about 0.3% by weight. Suitable preservatives for use herein include sodium benzoate and propyl paraben, and mixtures thereof.

The cosmetic compositions of the present invention can be in the form of foundations, blushers, concealers, compact powders, and the like, preferably as foundations and concealers.

The table below shows examples of cosmetic compositions of the present invention.

|  | I/% | II/% | III/% | IV/% | V/% |
|---|---|---|---|---|---|
| A |  |  |  |  |  |
| Cyclomethicone [DC 21330][1] | 15.2 | 16.0 | 14.8 | 15.3 | 15.7 |
| Cyclomethicone/Dimethicone copolyol [90:10] [DC3225C][1] | 15.0 | 16.5 | 18.5 | 15.2 | 17.25 |
| B |  |  |  |  |  |
| Mica | 0.1 | 0.15 | 0.1 | 0.12 | 0.1 |
| Titanium Dioxide (Cardre 70429)[2] | 8.25 | 9.6 | 14.2 | 7.85 | 8.5 |
| C |  |  |  |  |  |
| Yellow iron oxide | 0.55 | 0.6 | 0.49 | 0.59 | 0.58 |
| Red iron oxide | 0.3 | 0.25 | 0.28 | 0.24 | 0.4 |
| Black iron oxide | 0.1 | 0.08 | 0.08 | 0.12 | 0.15 |
| D |  |  |  |  |  |
| Durachem | 0.1 | 0.1 | 0.1 | 0.1 | 0.1 |
| Waxenol | 0.3 | 0.3 | 0.3 | 0.3 | 0.3 |
| E |  |  |  |  |  |
| Cyclomethicone [DC 21330][1] | 1 | 1.5 | 1 | 1.2 | 1 |
| Thixin R[3] | 0.3 | 0.3 | 0.3 | 0.3 | 0.3 |
| F |  |  |  |  |  |
| Ethylene Brassylate | 0.1 | 0.1 | 0.1 | 0.1 | 0.1 |

-continued

| | I/% | II/% | III/% | IV/% | V/% |
|---|---|---|---|---|---|
| G | | | | | |
| Ethanol | 4 | 8 | 5 | 6 | 5 |
| Polyvinylpyrrolidone [Luviskol K 17][4] | 1 | 1.8 | 0.8 | 1.5 | 1.2 |
| Salicylic acid | 1 | 2 | 1.5 | 1 | 1 |
| Dipropylene glycol | 10 | 12 | 11 | 10 | 11 |
| Glycerine | 10 | 10 | 9.5 | 12.5 | 9.8 |
| Carbowax 400 (PEG 8)[5] | 3.0 | 2.5 | 2.8 | 0 | 0 |
| H | | | | | |
| Deionised water | — | — | to 100 | — | — |
| Na$_4$ EDTA | 0.1 | 0.1 | 0.1 | 0.1 | 0.1 |
| Sodium Citrate | 0.3 | 0.25 | 0.25 | 0.32 | 0.3 |
| Sodium Chloride | 0.3 | 0.3 | 0.3 | 0.3 | 0.3 |

[1]Supplied by Dow Corning Corporation
[2]Supplied by Cardre Incorporated
[3]Trihydroxystearin, supplied by NL Chemicals
[4]Supplied by BASF
[5]Supplied by Union Carbide The formulations of Examples I to V can be prepared as follows. The various components listed in the Table have been segregated into groups, the constituents of each group being mixed together before being added to members of the remaining groups in accordance with the procedures set forth below.

In the first step, the mixture of components of phase A is stirred for approximately 5 minutes with shear mixing until homogeneous. With high speed shear mixing, the materials of phase B are added gradually to A and the batch is mixed for 20 minutes. Phases C and D are added and the resulting mixture is ground until fully dispersed.

The components from phase C are then added and the resulting mixture is ground until fully dispersed.

The waxy phase D is then added and the batch is heated to 85° C. in a water bath. When the waxes have melted, the batch is removed from the water bath and cooled to 50° C. Phase E premix is then added to the batch and homogenised for 10 minutes. The batch is cooled to room temperature. Phase F is added and the batch is homogenised for 10 minutes.

The water phase is prepared as follows. The components of phase H are mixed until dissolved. Phase G is prepared by adding PVP to the dipropylene glycol and mixing followed by addition with mixing of salicylic acid. Heating may be used if necessary. When most of the powder has dissolved, the glycerine is added to phase G while mixing, followed by addition of the Carbowax. Phase G is cooled and ethanol is added. The solution is mixed until clear. Phase H is added very slowly to phase G and mixed.

The water phase is finally added to the oil phase quickly whilst homogenising at a low speed, with stirring. When all of the water phase has been added, high shear is applied to the batch for approximately 5 minutes to increase the viscosity of the final product.

The resulting make-up composition is ready for packaging.

The cosmetic compositions of the Examples exhibit anti-acne efficacy, improved product stability and reduced hydrogen gas generation.

What is claimed is:

1. A cosmetic composition in the form of a water-in-oil emulsion, comprising:

(a) discontinuous aqueous phase comprising an aqueous or hydroalcoholic solution wherein said aqueous or hydroalcoholic solution comprises from about 0.1% to about 10%, by weight of the composition, of acidic skin care active;

(b) continuous oil phase; and (c) pigment which has been coated with organosilicon component selected from the group consisting of a polyorganosiloxane and a silane, and mixtures thereof; characterized in that the aqueous phase has a pH of from about 2.5 to about 4 such that the acidic skin care active exists significantly in protonated form and the coated pigment has a residual hydride content as measured by hydrogen potential of less than about 2.0 ml H$_2$/g of coated pigment.

2. A cosmetic composition according to claim 1 wherein the coated pigment has a residual hydride content as measured by hydrogen potential of less than about 1.0 ml H$_2$/g of coated pigment.

3. A cosmetic composition according to claim 1 wherein the aqueous phase has a pH of from about 1 to about 5.5.

4. A cosmetic composition according to claim 1 wherein the polyorganosiloxane is selected from the group consisting of (A) material of the formula:

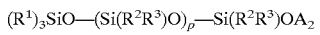
    $(R^1)_3SiO—(Si(R^2R^3)O)_p—Si(R^2R^3)OA_2$ wherein p is 1 to 1000, preferably from 1 to 100, A$_2$ is hydrogen or an alkyl group having from 1 to 30 carbon atoms, R$^1$ is a C$_1$–C$_{30}$ alkyl, R$^2$ and R$^3$ are independently selected from a C$_1$–C$_{30}$ alkyl and a phenyl; or (B) material of the formula:

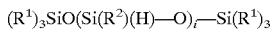
    $(R^1)_3SiO(Si(R^2)(H)—O)_i—Si(R^1)_3$ wherein i is 1 to 1000, and wherein R$^1$ and R$^2$ are as defined above for formula (A).

5. A cosmetic composition according to claim 1 wherein the silane is selected from the group consisting of material of the formula:

    $A_1SiX_1X_2X_3$    (C)

wherein A is an alkyl or alkenyl group having from 1 to 30 carbon atoms, and X$_1$, X$_2$ and X$_3$ are independently C$_1$–C$_4$ alkoxy.

6. A cosmetic composition according to claims 1 to 5 wherein the acidic skin care active is selected from the group consisting of salicylic acid, azelaic acid, retinoic acid, lactic acid, glycolic acid, pyruvic acid, and mixtures thereof.

7. A cosmetic composition according to claim 6 wherein the acidic skin care active is salicylic acid.

8. A cosmetic composition according to claim 7 comprising from about 0.1% to about 10%, by weight, of the acidic skin care active.

9. A cosmetic composition according to claim 1 comprising from about 0.1% to about 25%, by weight, of the organosilicon coated pigment.

10. A cosmetic composition according to claim 1 wherein the pigment is selected from the group consisting of iron oxide and titanium dioxide, and mixtures thereof.

11. A cosmetic composition according to claim 1 additionally comprising from about 0.1% to about 10%, by weight, of pyrrolidone-based solubilising agent.

12. A cosmetic composition according to claim 11 wherein the pyrrolidone-based solubilising agent is polyvinylpyrrolidone.

13. A cosmetic composition according to claim 1 additionally comprising from about 0.01% to about 5%, by weight, of citric acid or salt thereof.

14. A cosmetic composition according to claim 1 comprising from about 1% to about 50%, by weight, of volatile silicone oil selected from the group consisting of volatile silicones, non-volatile silicones and mixtures thereof.

15. A cosmetic composition according to claim 14 wherein the volatile silicone oil is selected from the group consisting of cyclic polyorganosiloxanes having viscosities of no greater than about 10 centistokes, and linear polyorganosiloxanes having viscosities of less than about 5 centistokes at 25° C., and mixtures thereof.

16. A cosmetic composition according to claim 15 wherein the volatile silicone oil is selected from the group consisting of cyclic polydimethylsiloxanes containing an average of from about 3 to about 9 silicon atoms and linear polydimethylsiloxanes containing an average of from about 3 to about 9 silicon atoms.

17. A cosmetic composition according to claim 16 wherein the polydiorganosiloxane-polyoxyalkylene copolymer is dimethicone copolyol.

18. A cosmetic composition according to claims 1 additionally comprising from about 0.1% to about 30%, by weight, of humectant.

19. A cosmetic composition according to claim 18 wherein the humectant is glycerine.

20. A cosmetic composition according to claim 14 comprising from about 0.1% to about 10%, by weight, of non-volatile silicones.

21. A cosmetic composition according to claim 1 comprising from about 20% to about 95%, by weight, of the oil phase, and from about 5% to about 80%, by weight, of the water phase.

* * * * *